(12) United States Patent
Eames et al.

(10) Patent No.: US 10,228,352 B2
(45) Date of Patent: Mar. 12, 2019

(54) DEVICE TO TEST AND AUTHENTICATE PRECIOUS METAL OBJECTS

(71) Applicants: Dexter Alan Eames, Cambridge, MA (US); Gary Arnold Eames, Falls Church, VA (US); Matt Ashford Eames, New York, NY (US)

(72) Inventors: Dexter Alan Eames, Cambridge, MA (US); Gary Arnold Eames, Falls Church, VA (US); Matt Ashford Eames, New York, NY (US)

( * ) Notice: Subject to any disclaimer, the term of this patent is extended or adjusted under 35 U.S.C. 154(b) by 348 days.

(21) Appl. No.: 14/661,466

(22) Filed: Mar. 18, 2015

(65) Prior Publication Data

US 2015/0308983 A1 Oct. 29, 2015

Related U.S. Application Data

(60) Provisional application No. 61/967,427, filed on Mar. 18, 2014.

(51) Int. Cl.
| | |
|---|---|
| *G01N 29/12* | (2006.01) |
| *G01N 29/30* | (2006.01) |
| *G01N 29/44* | (2006.01) |
| *G01N 33/20* | (2006.01) |
| *G01N 29/11* | (2006.01) |

(52) U.S. Cl.
CPC .......... *G01N 29/12* (2013.01); *G01N 29/11* (2013.01); *G01N 29/30* (2013.01); *G01N 29/4427* (2013.01); *G01N 33/20* (2013.01); *G01N 2291/0234* (2013.01); *G01N 2291/042* (2013.01); *G01N 2291/2698* (2013.01)

(58) Field of Classification Search
CPC ...................................... G01N 29/12

USPC .......................................................... 702/56
See application file for complete search history.

(56) References Cited

U.S. PATENT DOCUMENTS

| | | | | |
|---|---|---|---|---|
| 3,749,220 | A | | 7/1973 | Tabiichi |
| 4,234,071 | A | | 11/1980 | Le-Hong |
| 4,582,189 | A | | 4/1986 | Schmitt |
| 5,040,657 | A | * | 8/1991 | Gunn ....................... G07D 3/14 194/317 |
| 5,062,518 | A | * | 11/1991 | Chitty ...................... G07D 5/04 177/210 C |
| 5,551,542 | A | * | 9/1996 | Stockli ..................... G07D 3/14 194/334 |

(Continued)

FOREIGN PATENT DOCUMENTS

WO  WO-02103348 A1 * 12/2002 ............ G01N 29/22

OTHER PUBLICATIONS

Emerson Steed, Coin Identification Through Natural Frequency Analysis. Thesis, Brigham Young University, 2011.*

(Continued)

*Primary Examiner* — Joshua E Rodden

(57) ABSTRACT

The invention disclosed herein generally relates to a device and methods to authenticate the composition of materials, including, but not limited to gold and silver coins and gold and silver bars. The invention stimulates the natural frequencies of the tested object and then compares them to a reference dataset to confirm its authenticity. It achieves this through use of a transducer that both vibrates the object and collects amplitude response, allowing for consistent and highly accurate analysis across a broad spectrum, including ultrasonic frequencies.

8 Claims, 6 Drawing Sheets

(56) References Cited

U.S. PATENT DOCUMENTS

| | | | | |
|---|---|---|---|---|
| 5,591,913 | A * | 1/1997 | Tucker | G01N 29/12 |
| | | | | 73/602 |
| 6,079,262 | A * | 6/2000 | Palomeque | G07D 5/00 |
| | | | | 194/317 |
| 6,148,987 | A * | 11/2000 | Bernier | G07D 3/00 |
| | | | | 194/213 |
| 7,630,559 | B2 | 12/2009 | Ito | |
| 8,750,570 | B2 | 6/2014 | Kerschner | |
| 8,820,648 | B2 | 9/2014 | Shankman | |
| 8,903,675 | B2 * | 12/2014 | Jauriqui | G01N 29/043 |
| | | | | 702/124 |
| 9,304,112 | B2 * | 4/2016 | Rhodes | G01N 29/12 |
| 2015/0300993 | A1 * | 10/2015 | Prest | G01N 29/12 |
| | | | | 148/508 |

OTHER PUBLICATIONS

Mary D Waller, Vibrations of Free Circular Plates. Part 1: Normal Modes. Physical Society, 1937, vol. 50, 70-76.
Pouladkhan, AR et al, The Vibration of Thin Plates by Using Modal Analysis. World Academy of Science, Engineering and Technology, 2011, vol. 59, 2880-2885.
Thomas Michael Juliano, The Computer Evaluation of the Natural Frequencies of Vibrating Circular Plates. Thesis, Newark College of Engineering, 1970.
The Fisch Coin Tester. http://thefisch.com/.
Coin Trust App http://www.cointrustapp.com/en/index.php.
Ultrasonic Testing of Gold Bars http://www.olympus-ims.com/en/applications/ut-testing-gold-bars/.
X-Ray Fluorescence http://www.bruker.com/products/x-ray-diffraction-and-elemental-analysis/handheld-xrf/applications/mining/xrf-gold-testing.html?gclid=CJXQ2_fhz8MCFUWWtAodYTU.

\* cited by examiner

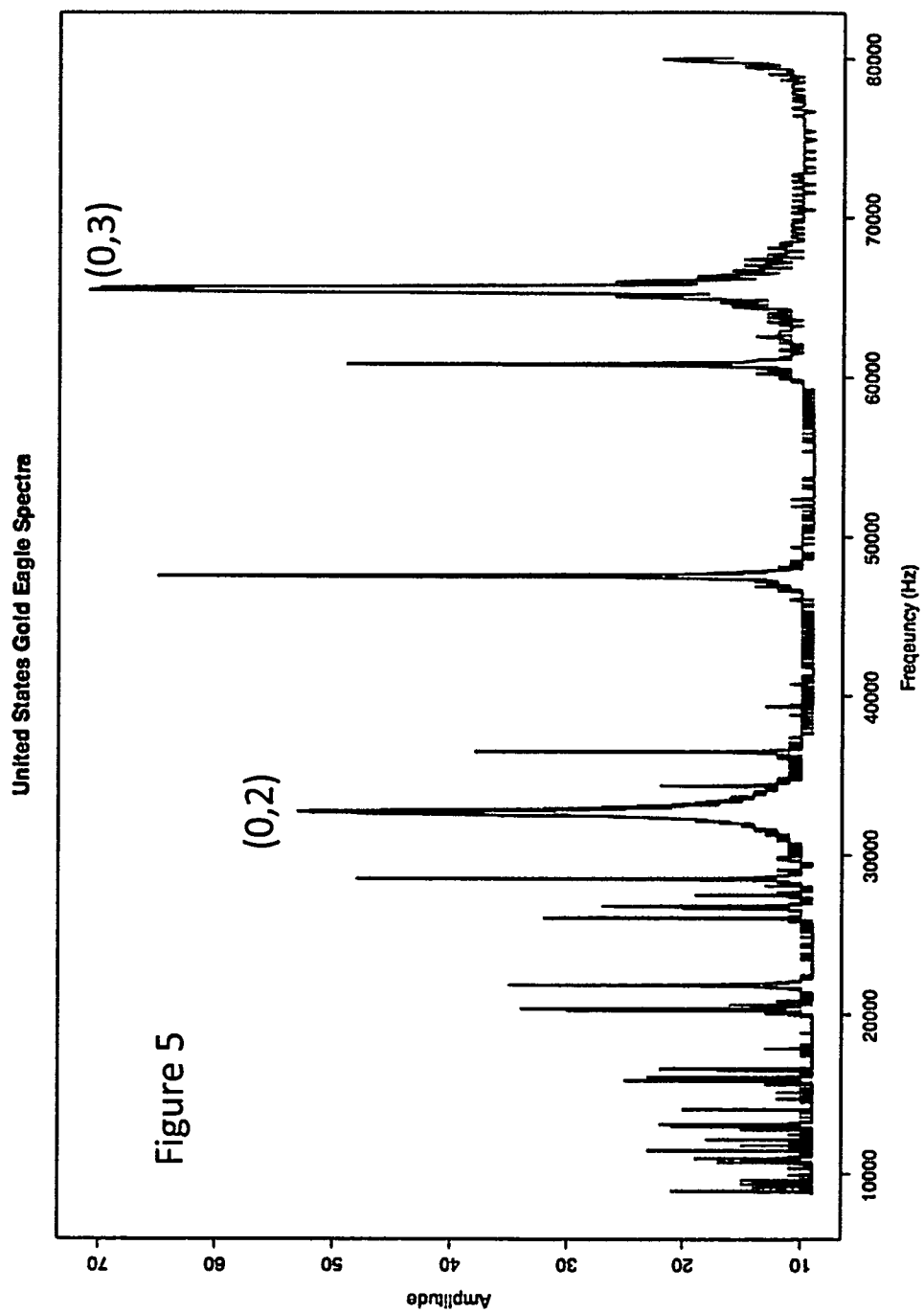

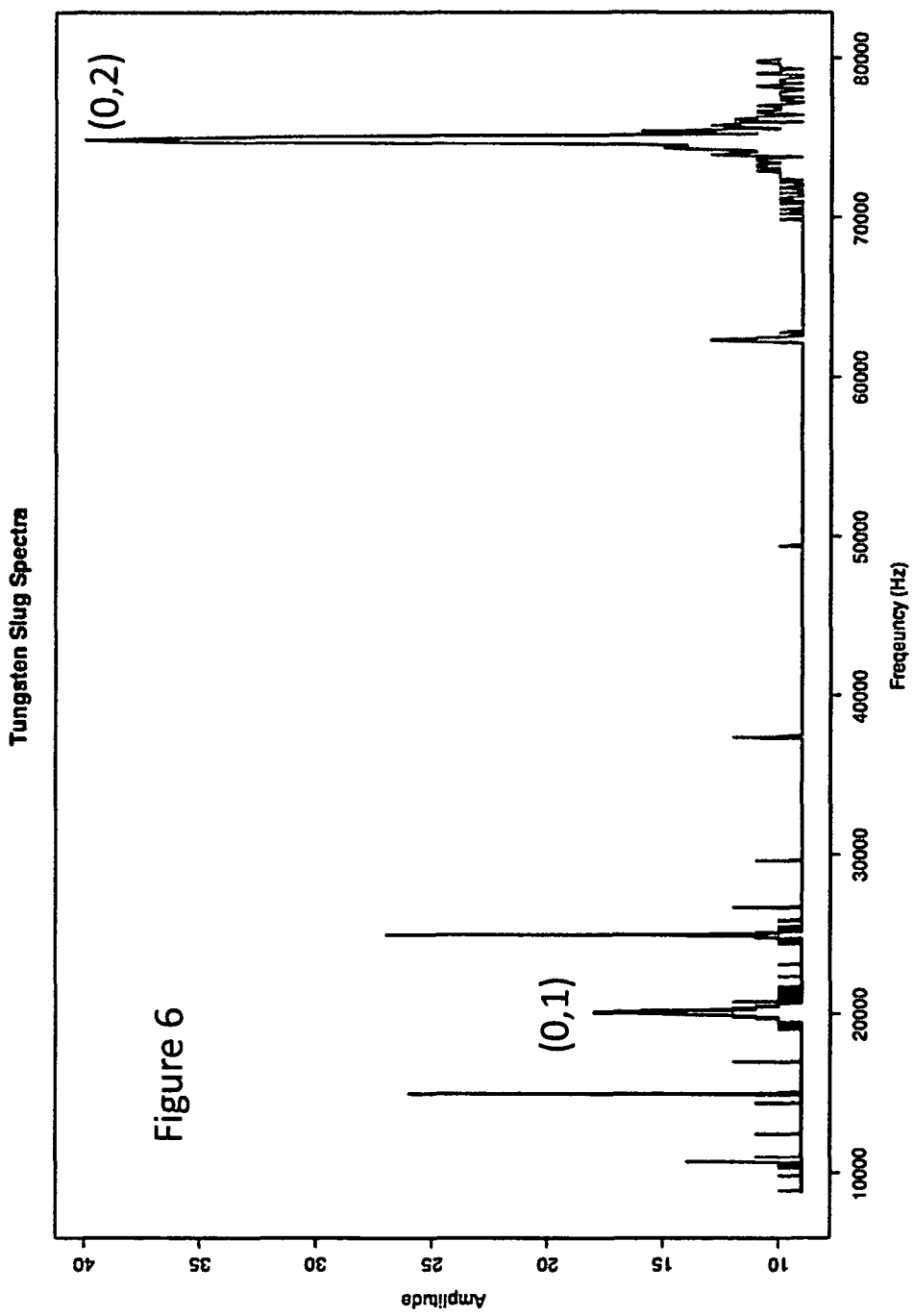

DEVICE TO TEST AND AUTHENTICATE PRECIOUS METAL OBJECTS

FIELD OF THE INVENTION

The invention disclosed herein generally relates to a device and methods to authenticate the composition of materials, including, but not limited to gold and silver coins and gold and silver bars.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

High value materials, including gold and silver coins and bars, have long been targets for counterfeiters. As such, there has existed a need for a non-destructive method that can ascertain the authenticity of the material composition. Such an approach must not only test the surface of the material, but must also assess its unseen interior as well.

One of the oldest methods to determine the composition of materials is the so-called "Archimedes method," which evaluates the volume and mass of an object to determine its density. Since gold has an abnormally high density (19.30 $g/cm^3$), this approach has been used to evaluate the authenticity of gold coins and bars. However, there are other materials with a similarly high density, including tungsten (19.25 $g/cm^3$), which is worth roughly $\frac{1}{1000}$ the price of gold, and also depleted uranium (19.05 $g/cm^3$). These cheap alternatives can be used in the core of gold coins and bars by counterfeiters to devalue the materials, and cannot be detected by the Archimedes method. While these substitutes have slightly lower densities than gold, they can be complimented by the addition of small amounts of heavier, more expensive elements, such as rhenium, platinum, and osmium. In 2010, fake gold bars were discovered in Hong Kong that featured a pure gold exterior with an interior comprised of a complex alloy of gold, osmium, iridium, ruthenium, copper, nickel, iron, and rhodium.

Another approach to nondestructively determine the authenticity of a material is X-ray fluorescence. This method works by analyzing the secondary X-rays from a material that has been bombarded by high-energy X-rays or gamma rays, and can be used very precisely in elemental analysis. Unfortunately, the penetration depth of X-ray fluorescence is small, ranging from µm to mm, thus making it unable to analyze the materials comprising the core of coins and bars.

Ultrasonic testing can also be used for elemental analysis. However, ultrasonic testing requires a large flat surface for the probe to make contact with. In the case of coins, surface features that are irregular in shape make analysis all but impossible. Furthermore, depending on how and where the tungsten is embedded, it may not be detected by ultrasound.

Consequently, there exists a need for nondestructive means to nondestructively determine the authenticity of materials.

SUMMARY OF INVENTION

The current invention is designed to test and verify the authenticity of high value objects by assessing their natural frequencies and validating them against previously stored reference data.

In some embodiments of the invention, high value objects may comprise coins, ingots, bars, jewelry, and other objects produced in a wide range of shapes and sizes. Materials from which these high value objects are made may comprise precious metals such as gold, crown gold, silver, platinum, copper, rhodium, iridium, palladium, osmium, rhenium, ruthenium, germanium, beryllium, gallium, indium, tellurium, mercury, bismuth, or alloys thereof.

In some embodiments of the invention, coins comprise those minted in different nationalities, including but not limited to United States Gold Eagles, United States American Buffalos, United States Double Eagles, South African Krugerrands, Austrian Philharmonics, United Kingdom Britannias, United Kingdom Sovereigns, Canadian Gold Maple Leafs, Chinese Pandas, Gold Dinars, Malaysian Kijand Emas, Russian Cherbonets, Russian George the Victorious, Swiss Vrenelis, French Napoleons, Australian Gold Nuggets, Australia Lunar Series I & II, Israel Tower of Davids, Kazakhstan Golden Ibris, Mexico Gold Libertads, Mexico Centenarios, Poland Orzel Bieliks, Poland Bene Merentibus, Somalia Gold Elephants, Ukraine Archangel Michaels, Canadian Palladium Maple Leafs, Australian Platinum Koalas, Australia Platinum Platypus, Canadian Platinum Maple Leafs, Isle of Man Nobles, Mexico Platinum Libertads, United States Platinum Eagles, Armenia Noah's Arks, Australia Great White Sharks, Australia Kangaroos, Australia Silver Koalas, Australia Silver Kookaburras, Australia Lunars, Australia Saltwater Crocodiles, Austria Vienna Philharmonics, Benin Elephants, Cameroon Cross-River Gorillas, Canadian Arctic Foxes, Canadian Birds of Prey, Canadian Grey Wolfs, Canadian Silver Maple Leafs, Canadian Polar Bears, Canadian Wildlife Series, Chinese Lunars, Chinese Silver Pandas, Congo African Lions, Congo Baby Lions, Congo Rhinoceros, Cook Islands Young Wildlife Series, Fiji Eagles, Fiji Otter Lutras, France Silver Coins, Gabon Elephants, Gabon Lions, Kazakhstan Silver Irbis, Mexico Silver Libertads, Mongolian Argalis, Mongolian Long-Eared Hedgehod, Mongolian Manuls, Mongolian Scorpions, Mongolian Ural Owls, Mongolian Wolverines, New Zealand Kiwis, Niue Secrets of Lichtenstein, Palau Red Squirrel Swarovskis, Papua New Guinea Spiny Anteaters, Russian Silver Saint George the Victorious, Russian Southwest Asian Leopards, Somalia Silver Elephants, South Africa Marine Protected Areas, South Africa Surinames, Togo Bison D'Europe, Tokelau Crocidiles, Turkey Street Stray Animals, Urkaine Silver Archangel Michaels, United Kingdom The George and the Dragons, United Kingdom Silver Britannias, United States America the Beautifuls, and United States Silver Eagles.

In some embodiments of the invention, coins may comprise those minted currently or previously in history.

In some embodiments of the invention, coins may comprise those of different sizes or denominations, including but not limited 1 ounce, $\frac{1}{20}^{th}$ ounce, $\frac{1}{10}^{th}$ ounce, $\frac{1}{4}^{th}$ ounce, $\frac{1}{2}$nd ounce, 2 ounces, 5 ounces, 10 ounces, 1 kilogram, 10 kilograms, 100 kilograms, 0.1867 ounce, 1.2065 ounce, 0.0933 ounce, 0.9675 ounce, 0.2489 ounce, and 15.71 grams.

In some embodiments of the invention, bars or ingots may comprise those produced by any fabricator, bank, nationality, manufacturer, or mine. Sizes may include, but are not limited to 1 ounce, 5 ounces, 10 ounces, 20 ounces, 30 ounces, 50 ounces, 100 ounces, ½ gram, 1 gram, 2 grams, 20 grams, 50 grams, 100 grams, 250 grams, 500 grams, 1 kilogram, or 10 kilograms.

In some embodiments of the invention, previously stored reference data may be comprised of previous measurements of multiple standards.

In some embodiments of the invention, previously stored reference data may be comprised of values predicted by theory.

In some embodiments of the invention, previously stored reference data may be comprised of values predicted by finite element analysis.

In some embodiments of the invention, comparison of measured sample data against previously stored reference data may be assessed by determining the presence or absence of specific peaks. In some embodiments, the presence of a specific peak may be determined by whether a defined intensity threshold is crossed within a defined range of frequencies. In other embodiments, peak identification algorithms may be used to this purpose.

In some embodiments of the invention, comparison of measured sample data against previously stored reference data may be assessed by using machine learning algorithms, where the stored reference data is the training dataset.

In some embodiments of the invention, the peaks used to identify the measured sample correspond to normal modes of vibration in a disc. These modes may be comprised of, but not limited to, (2,0), (0,1), (3,0), (1,1), (4,0), (5,0), (2,1), (0,2), (6,0), (3,1), (1,2), (7,0), (2,2), (4,1), (8,0), (0,3), and (5,1).

In some embodiments of the invention, the object is mechanically struck and the resultant vibrations are recorded with an ultrasonic microphone. By taking a Fast Fourier Transform of the recordings, the resultant spectra of the tested object, comprised of natural frequencies and other peaks can be obtained.

In some embodiments of the invention, the objected is vibrated by a transducer. The transducer may sweep a spectrum of frequencies or selectively target frequencies with known peaks. The transducer may produce a single pulse, or it may oscillate with a sine wave, square wave, triangle wave, or other wave functions. After vibrating the object, the transducer can then measure the intensity and persistence of vibration in the object when it is no longer being driven.

In some embodiments of the invention, a centering apparatus will be used to ensure the tested object will be in contact with the transducer in a consistent fashion. This centering apparatus may be constructed so that it can accommodate multiple objects of different sizes. If the tested object is a coin, the centering apparatus may be used to guide the coin into position though tracks contacting the inner lip of the rim, the face of the rim, or the outer lip of the rim or the reeded, ridged, or grooved edges.

In some embodiments of the invention, when the tested object has a symmetrical shape, such as a coin or bar, the centering apparatus will be constructed so that the transducer makes contact with the center of the tested object.

In some embodiments of the invention, the device will comprise more than one transducer, including one for driving the vibration and one for measuring resonance.

In some embodiments of the invention, the object itself will be identified based on its resultant spectra.

In some embodiments of the invention, the user identifies the object to be tested, which in turns selects the appropriate previously recorded reference data for comparison.

BRIEF DESCRIPTION OF THE DRAWINGS

FIG. 5. An example of a measured spectra, from 8500 Hz to 80000 Hz, of a United States Gold Eagle.

FIG. 6. An example of a measured spectra, from 8500 Hz to 80000 Hz, of a tungsten slug of nearly identical dimensions to a United States Gold Eagle.

DETAILED DESCRIPTION OF THE INVENTION

Figure 1:
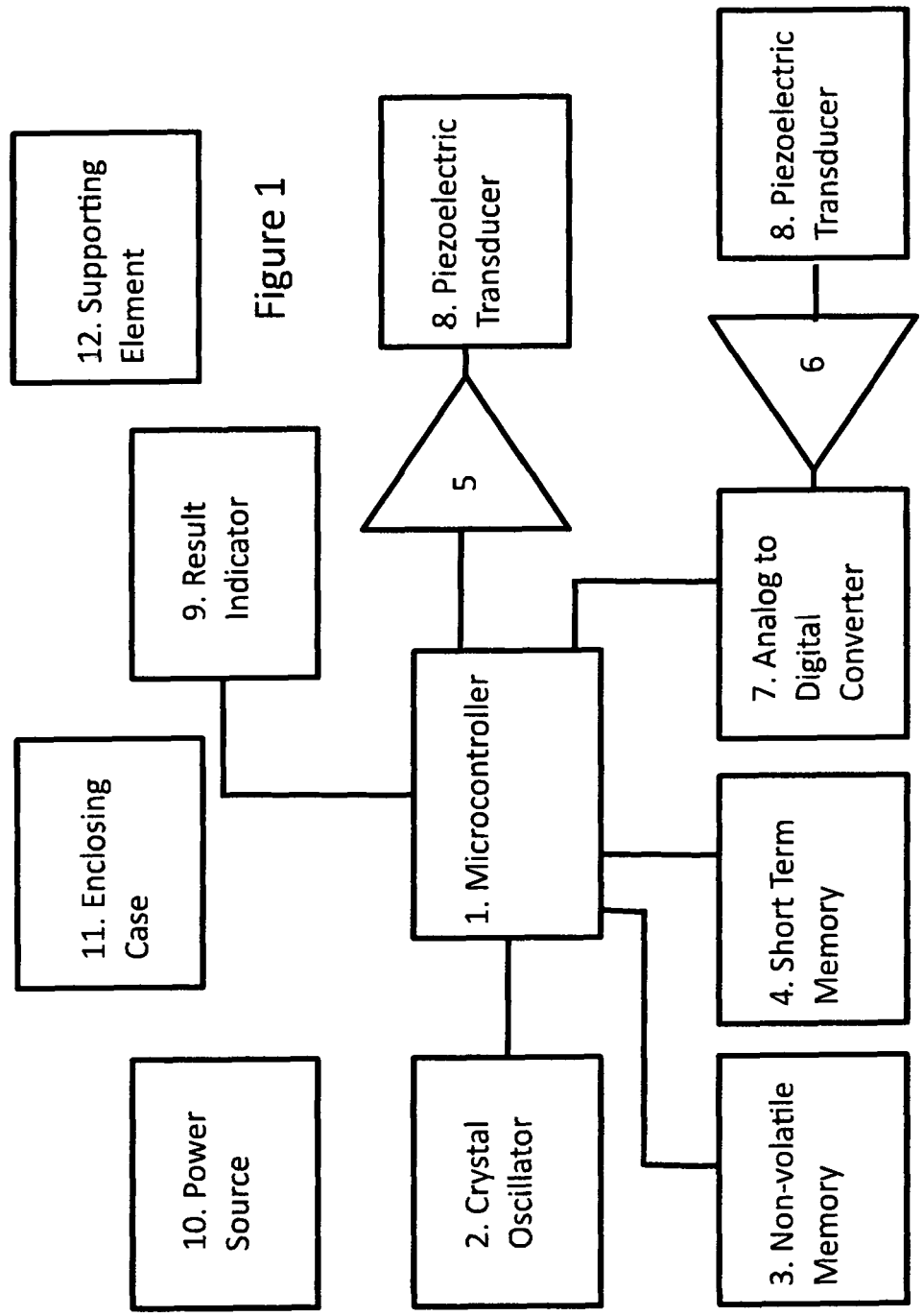
FIG. 1. A block diagram of one embodiment of the invention, comprising 1) a programmed digital microcontroller, 2) a crystal oscillator, 3) a memory for non-volatile data storage, 4) a memory for temporary data storage, 5) electronic circuits for amplifying the driving signals from the microcontroller to a piezoelectric transducer, 6) electronic circuits for amplifying electric signals produced by mechanical vibrations operating upon a sensing piezoelectric transducer, 7) a means for digitizing the amplified electrical signals from the sensing piezoelectric transducer, 8) one or two piezoelectric transducers, 9) a means of signaling the results of the tests to a user, 10) batteries or other source of power along with voltage converters to provide appropriate voltages for the various components, 11) an enclosing case.
Figure 2:
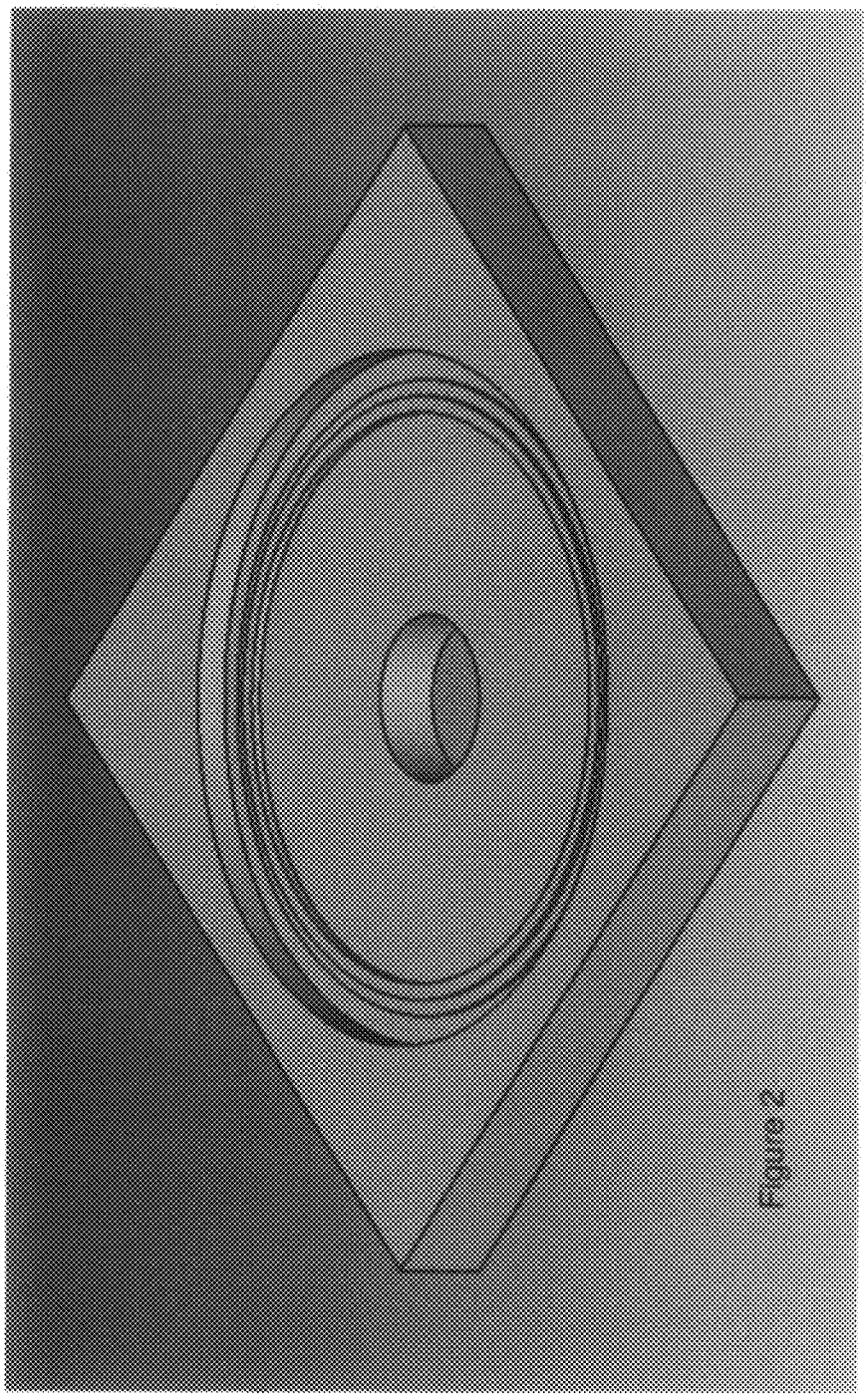
FIG. 2. One example of a centering apparatus, in this case designed to accommodate coins of multiple sizes and countries of origin. This design can center a Canadian Gold Maple (along the inner track), a Chinese Gold Panda (along the inner rim of the outer track), and United States Gold Eagles and South African Krugerrands (along the outer rim of the outer track) by use of concentric circles of various heights and widths that correspond to the geometries of these coins. A slight depression exists in the center of the device to accommodate surface features of the coins. The hole in middle will accommodate the transducer.
Figure 3:
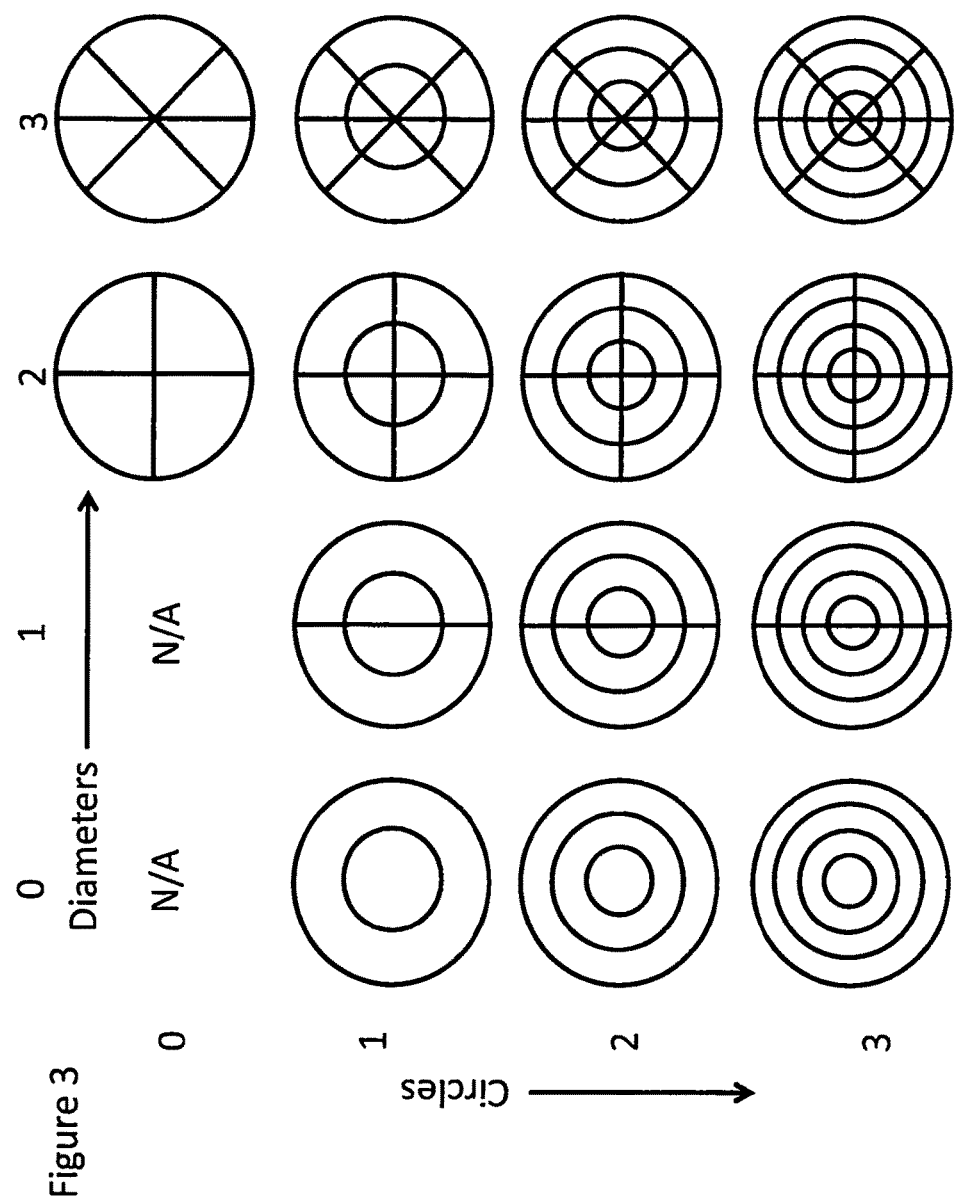
FIG. 3. The Chladni patterns of vibration of thin circular plates. Each drawing corresponds to the pattern of vibration at a specific natural frequency. For thin circular plates, the (2,0) mode is the fundamental node. In mode notation, the first number corresponds to the number of "diameter" oscillation nodes, and the second number corresponds to the number of "circle" oscillation nodes.
Figure 4:
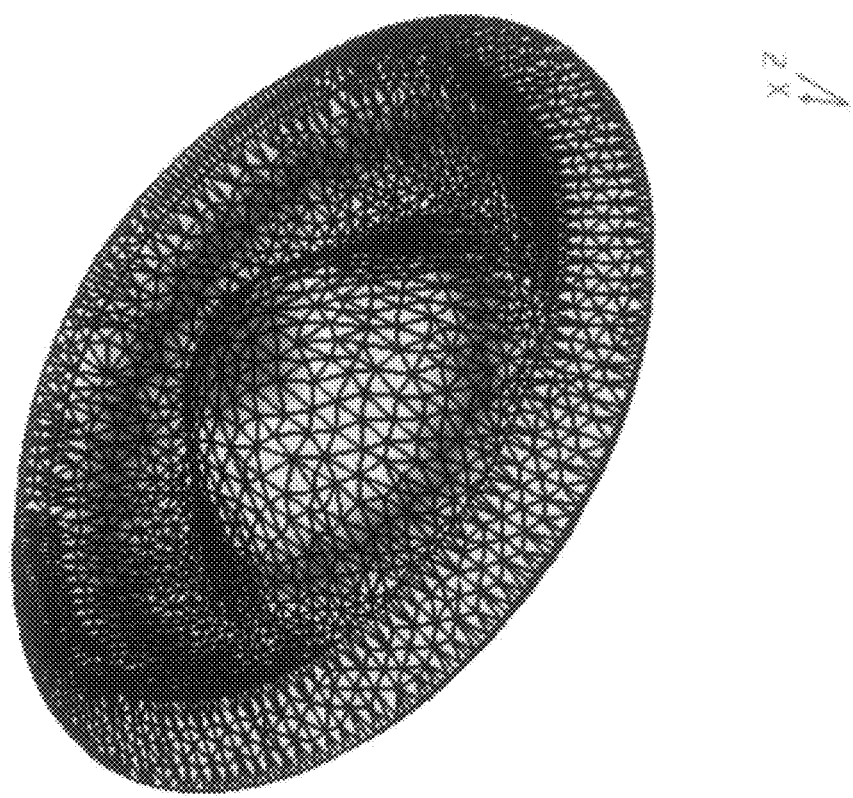
FIG. 4. An example of a natural frequency predicted by Finite Element Analysis for a coin-shaped object made of gold. Deformations have been scaled up for easier visualization. In this figure, the predicted natural frequency corresponds to the (0,2) mode.

While various methods of striking a coin and listening to the audible sound waves have been proposed for coin identification, the present inventors are unaware of any method that drives vibration at specific frequencies with a transducer, and measures the resonance at said frequencies with a transducer. The advantages of such an approach are numerous.

First, it completely eliminates user-induced variability and error. All previously proposed methods involve tapping a coin held in the hand or dropping it on a surface, and recording the sound with a microphone. These approaches are uncontrolled and will introduce significant variability to the results. For example, how tightly held the coin is, what it is struck with, where the coin is struck, what type of surface the coin is dropped on, where the coin lands—all of these considerations will have a profound effect on the spectra. In contrast, a coin in direct contact with a transducer, will produce a highly consistent, highly reproducible signal regardless of user.

Second, ignoring the difficulty posed by having a user operate a microphone while manually striking a coin, collecting a signal in this approach is extremely problematic. A microphone will not merely collect the sound of the coin vibrating, but it will also capture the vibration of whatever the coin struck, as well as all other environmental sounds—in short, noise. A transducer, on the other hand, in direct contact with an object will only measure the vibration of that object, thus drastically reducing external noise.

Third, microphones in the aforementioned proposed methods have an upper limit of detection of 20 kHz. For a standard 1 oz United States Gold Eagle, the vast majority of normal modes of vibration are beyond this limit. For objects of other dimensions, all of the natural frequency modes may exist beyond this limit. Furthermore, the separation between peaks becomes substantially larger at higher modes of vibration. For example, the difference between the first natural frequency (2,0) of the 1 oz United States Gold Eagle and the 1 oz South African Krugerrand is a few hundred Hz, whereas the difference between their respective (0,3) modes of vibration is a few thousand Hz. When attempting to discern the presence of low-percentage impurities, this improved resolution is critical.

Here, we describe a device capable of consistent, high-resolution elemental analysis. This invention can be used to test and verify the authenticity of high value objects such as coins, but also other shapes as well. The invention may work with objects made of different types of materials, including but not limited to precious metals such as gold. In one implementation the invention may authenticate high value objects that are produced in a standard form, such as minted coins. This implementation of the invention may be programmed to recognize only those types of objects for which it has previously stored data. In another implementation the invention may authenticate the elemental material of objects such as ingots or bars of precious metals produced in a wide range of sizes and shapes.

The invention may comprise 1) a programmed digital microcontroller, 2) a crystal oscillator, 3) a memory for non-volatile data storage, 4) a memory for temporary data storage, 5) electronic circuits for amplifying the driving signals from the microcontroller to a piezoelectric transducer, 6) electronic circuits for amplifying electric signals produced by mechanical vibrations operating upon a sensing piezoelectric transducer, 7) a means for digitizing the amplified electrical signals from the sensing piezoelectric transducer, 8) one or two piezoelectric transducers, 9) a means of signaling the results of the tests to a user, 10) batteries or other source of power along with voltage converters to provide appropriate voltages for the various components, 11) a supporting element designed to consistently hold the tested object in the same orientation next to the transducer, 12) an enclosing case.

In an implementation for testing coins the case may be constructed to allow the coin under test to be set flat upon three points, one or two of which may be piezoelectric transducers. In one implementation of the invention a single transducer operates as both the driving and the sensing transducer. In a second implementation, one transducer is the driving element and a second transducer is the sensing element. Microcontrollers commercially available may contain some of the functions shown as separate items, such as the means for digitizing or a memory.

To validate tested objects, acquired data from the test sample will be compared to a saved reference standard. The reference standard may be generated by analyzing copies of the test object. The number of tested copies may be 10, 20, 50, 100, 500, 1000, or any number necessary to reliably predict the spectra. More sophisticated methodologies may be incorporated to classify spectra, including machine learning.

Different types of transducers and designed circuits might produce slightly different measured values for natural frequencies. Each device may be standardized with a reference dataset according to its previously measured natural frequencies.

Spectra from tested objects may also be compared to those expected from theoretical modeling. The equation for motion for bending or flexural waves in a thin plate (comparable to a minted coin) is as follows:

$$\partial^2 z/\partial t^2 + [Eh^2 12\rho(1-v^2)]\nabla^4 z = 0 \quad (1)$$

Where $\rho$ is density, E is Young's modulus, v is Poisson's ratio, and h is the plate thickness. For harmonic solutions:

$$z = Z(x,y)e^{j\omega t} \quad (2)$$

$$\nabla^4 Z - [12\rho(1-v^2)\omega^2/Eh^2]Z = \nabla^4 Z - k^4 Z = 0 \quad (3)$$

Where:

$$k^2 = \omega(12)^{1/2}/c_L h \quad (4)$$

Where $c_L$ is the velocity of longitudinal waves in an infinite plate. The velocity of bending waves in a plate depends on the frequency:

$$v(f) = \omega/k = (1.8 f h c_L)^{1/2} \quad (5)$$

The frequency of a bending wave is proportional to $k^2$:

$$f = \omega/2\pi = 0.0459 h c_L k^2 \quad (6)$$

The values of k that correspond to the normal modes of vibration depend on the boundary conditions. For a plate with a free edge—such as a coin resting atop a transducer—these equations are difficult to solve mathematically. The fundamental frequency is estimated to be approximately:

$$f(2,0) = 0.2413 c_L h/a^2 \quad (7)$$

Where a is the radius of the disc. Higher modes of natural frequency are predicted to occur at specific ratios relative to the fundament, though the values of these ratios vary from one reference to the next. We have found in this work that these values can vary according to the material and dimensions of the disc, but are consistent among objects with the same composition and similar dimensions.

Spectra from tested objects may also be compared to those predicted by Finite Element Analysis (FEA). Test objects may first be modeled with Computer-aided design (CAD) software, or may be mapped with a 3D-scanner. During FEA, a mesh framework may be applied to the 3D structure. Additionally, boundary conditions and elemental composition may be added to the model. When the parameters have been selected to best represent testing conditions, the FEA may be run to predict the natural frequencies of the test object.

In some embodiments of the invention, a 3D-scanner and FEA software are combined with the transducer, so that predicted natural frequencies can be compared to those measured for objects with nonstandard topologies, such as jewelry.

In some embodiments of the invention, the test may use a multiplicity of driving signals created by the microcontroller from the crystal oscillator time base. The driving signals may consist of sustained oscillations at precise frequencies. The driving signals may be amplified and transmitted to the driving piezoelectric transducer causing it to oscillate at the precise frequencies. The driving transducer may be in direct physical contact with the object under test. If the object under test has a natural resonance that is sympathetic to the driving oscillation, then the object may vibrate in response to the driving signal. The sensing piezoelectric transducer may also be in direct physical contact with the object under test. The electric signals generated by the sensing transducer responding to oscillations of the object under test may be amplified and transmitted to the means of digitizing the signal. The digitized signals may be stored by the microcontroller during the test in the memory for temporary storage. By measuring across a spectrum of frequencies, natural resonances of the object under test can be identified, and compared to results previously stored in the non-volatile memory from a known authentic object. The spectrum of frequencies tested can include the audio range and the ultrasonic range. The natural resonances of an object are a function of the material and shape of the object, and said resonances would be difficult to replicate in an object that was not genuine.

In some embodiments of the invention, the test may use a single type of driving signal created by the microcontroller from the crystal oscillator time base. The driving signal may consist of a short burst at a precise ultrasonic frequency. The frequency of the driving signal may be such that its wavelength in the coin material may be shorter than the physical dimensions of the object under test. The driving signal may be amplified and transmitted to the driving piezoelectric transducer causing it to oscillate at the precise ultrasonic frequency. The driving transducer may be in direct physical contact with the object under test. The ultrasonic signal may enter the object under test and reflect within the object. The sensing piezoelectric transducer may also be in direct physical contact with the object under test. The sensing transducer may respond to the ultrasonic signal within the object and generate an electric signal proportional it. This electric signal may be amplified and transmitted to the means for digitizing the signal. The digitized signals may be stored during the test by the microcontroller in the memory for temporary storage. In one implementation of the invention this stored signal may be compared to results previously stored in the non-volatile memory from known authentic objects. The digitized signal will be a function of the material and the shape of the object, and said signal would be difficult to replicate in an object that was not genuine. In another implementation of the invention the signal from the sensing transducer may be analyzed to extract the speed of sound in the material, and the homogeneity of the material. While this test is similar to an ultrasonic thickness measurement, this test may have added functionality compared to a thickness measurement, since the proposed invention may not assume that the object under test is made from homogeneous material. The proposed invention will be able to determine if the object under test is made from homogeneous material. A further improvement over an ultrasonic thickness gauge may be the ability to measure the speed of transmission of the signal within the material.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Device for gold coin authentication. The device will feature a single transducer that is surrounded by concentric circles or "tracks" used to center different gold coins of different sizes. The tracks are removable and can be attached by a simple snapping apparatus in order to accommodate different tracks built for other coins of various dimensions. The tracks also include metal contacts so that the device is powered on when a coin is placed on the device. The user will identify the type of coin they are testing by dialing a switch. If the tracks are selectable, then the type of coin can be embedded in the track, as for example a specific resistance that is read by the microcontroller. The transducer itself will then selectively oscillate at specific frequencies that are known to make the targeted coin resonate, including the (0,2) and (0,3) modes of vibration. Additionally, the transducer will also sweep frequencies known to not have any resonance for the tested coin to further confirm its identity. If all the criteria are met, the device will give a positive identification signal. If even one of the criteria is not satisfied, the device will indicate a false sample.

Example 2

Device for gold bar authentication. The device will feature a single transducer that is surrounded by rectangular track used to center a gold bar. A mechanically-driven, precision-guided mallet will then strike the bar, and the ultrasonic audio spectra will be analyzed and compared to the expected spectra for the specified bar.

Example 3

Device for gold coin authentication. The device will be specifically designed to accommodate 1 oz United States Gold Eagles, 1 oz South African Maples Krugerrands, 1 oz Chinese Gold Pandas, and 1 oz Canadian Gold Maples. The device will feature a single transducer that is surrounded by concentric circles or "tracks" used to center different gold coins of different sizes. These tracks will correspond to the inner diameter of the Maple (0.56") and Panda (0.59"), as well as the outer diameter of the Eagle and Krugerrand (0.645"). As the rim of Panda is wider than the other coins, its track will be further recessed than the others. Additionally, there will be a center recession to accommodate the surface features of all the coins. Using this setup, the spectra of each coin will be measured from 8500 Hz to 80000 Hz. For the Eagle, the following peaks were detected: (0,2) 32000-33000, (0,3) 65000-66000, (3,0) 11500-12500, (4,0) 20000-21000, (5,0) 28000-29000, (6,0) 36000-37000, (7,0) 47000-48000, (8,0) 60500-61500. For the Krugerrand, the following peaks were detected: (0,2) 34000-35000, (0,3) 68500-69500, (3,0) 12000-13000, (4,0) 22500-23500, (5,0) 265000-28000, (6,0) 37500-38500, (8,0) 63000-64000. For the Maple, the following peaks were detected: (0,2) 32000-33000, (0,3) 64000-65000, (3,0) 10500-11500, (4,0) 21000-22000, (5,0) 30000-31000, (7,0) 46500-47500. For the Panda, the following peaks were detected: (0,2) 25500-26500, (0,3) 53500-54500, (3,0) 10500-11500, (4,0) 17500-18500, (7,0) 38500-39500, (8,0) 51000-52000. The test coin will be placed onto the track and the user will identify it by a switch, will draw up the corresponding reference dataset. The spectra ranges will be scanned and peak identification software will be used to confirm the presence the natural frequencies. If all the criteria are met, the device will give a positive identification signal. If even one of the criteria is not satisfied, the device will indicate a false sample.

We claim:

1. A device for authenticating the composition of a test substance by using resonant ultrasound spectroscopy to determine a plurality of resonant frequencies of the test substance and comparing the plurality of resonant frequencies to one of a plurality of reference standards, comprising:
   (a) a plurality of reference standards each corresponding to one of a plurality of substances, each reference standard comprising natural frequencies for the corresponding one of the plurality of substances, the natural frequencies comprise the (0,2), (0,3), (3,0), (4,0), (5,0), (6,0), (7,0), and (8,0) modes;
   (b) a single transducer configured to both vibrate a test substance and measure a response from the test substance, the single transducer configured to vibrate the test substance, stop, measure the response when the transducer is no longer being vibrated, and continually repeat this process for each of the natural frequencies corresponding to a single one of the reference standards for which the authenticity of the test substance is being tested;
   (c) peak analysis algorithms determining resonant frequencies of the test substance based upon the response to the transducer to vibrate the test substance at the natural frequencies in the reference standard which corresponds to the substance for which the test substance is being compared, and comparing the resonant frequencies to the natural frequencies of the reference standard and determining an authenticity of the test substance.

2. The device of claim 1, where in the test substance is a precious metal comprising at least one of gold, crown gold, silver, platinum, copper, rhodium, iridium, palladium, osmium, rhenium, ruthenium, germanium, beryllium, gallium, indium, tellurium, mercury, bismuth, or alloys thereof.

3. The device of claim 2, where the test substance is of standardized dimensions, and includes at least one of coins or bars.

4. The device of claim 3, wherein the test substance is coins, wherein the coins are guided into position by a series of concentric circles or "tracks" used to center different gold coins of different sizes.

5. The device of claim 1, wherein the transducer vibrates at frequencies ranging from 20,000 to 80,000 Hz.

6. The device of claim 1, wherein the reference standard is determined by measuring validated standards of the test substance.

7. The device of claim 1, wherein the reference standard is determined by the theory of natural frequency.

8. The device of claim 1, wherein the reference standard is determined by Finite Element Analysis.

* * * * *